United States Patent [19]
Groner et al.

[11] Patent Number: 5,534,409
[45] Date of Patent: Jul. 9, 1996

[54] CYTOKINE REGULATED TRANSCRIPTION FACTOR

[75] Inventors: Bernd Groner, Basel, Switzerland; Fabrice Gouilleux, Mulhouse, France; Hiroshi Wakao, Palo Alto, Calif.

[73] Assignee: Ciba-Geigy Corporation, Tarrytown, N.Y.

[21] Appl. No.: 366,276

[22] Filed: Dec. 29, 1994

[30] Foreign Application Priority Data

May 11, 1994 [GB] England .................................. 9409396

[51] Int. Cl.$^6$ ............................ C12Q 1/68; C12P 19/34; C07H 21/02; C07H 21/04
[52] U.S. Cl. ............................ 435/6; 435/91.2; 536/23.1; 536/24.3; 536/24.33
[58] Field of Search .................................. 536/24.3–.33, 536/23.1; 435/6, 91.2, 240.2, 0.3, 0.11, 172, 3, 69.1

[56] References Cited

PUBLICATIONS

Ali et al., "A Prolactin–dependent Immune Cell Line (Nb2) Express a Mutant Form of Prolactin Receptor", *J. Biol. Chem.* 266: 20110–20117 (1991).
Argetsinger et al., "Identification of JAK2 as a Growth Hormone Receptor–Associated Tyrosine Kinase", *Cell.* 74:237–244 (1993).
Bazan et al., "Structural design and molecular evolution of a cytokine receptor superfamily", *Proc. Natl. Acad. Sci. USA*, 87: 6934–6938 (1990).
Boutin et al., "Cloning and Expression of the Rat Prolactin Receptor, a Member of the Growth Hormone/Prolactin Receptor Gene Family", *Cell*, 53: 69–77 (1988).
Boutin et al., "Identification of a cDNA Encoding a Long Form of Prolactin Receptor in Human Hepatoma and Breast Cancer Cells", *Mol. Endocrinol*, 3(9): 1455–1461 (1989).
Cosman et al., " A new cytokine receptor superfamily", *Trends, Biochem. Sci.*, 15: 265–270 (1990).
D'Andrea et al., "The Cytoplasmic Region of the Erythropoietin Receptor Contains Nonoverlapping Positive and Negative Growth–Regulatory Domains", *Mol. Cell. Biol.*, 11(4): 1980–1987 (1991).
Davis, et al., "Expression of Multiple Forms of the Prolactin Receptor in Mouse Liver", *Mol. Endocrinol*, 3: 674–680 (1989).
Doppler et al., "Prolactin and glucocorticoid hormones synergistically induce expression of transfected rat β–casein gene promoter constructs in a mammary epithelial cell line", *Proc. Natl. Acad. Sci. USA*, 86: 104–108 (1989).
Edery et al., "Identification and sequence analysis of a second form of prolactin receptor by molecular cloning of complementary DNA from rabbit mammary gland", *Proc. Natl. Acad. Sci. USA*, 86: 2112–2116 (1989).
Fu et al., "The proteins of ISGF–3, the interferon α–induced transcriptional activator, define a gene family involved in signal transduction", *Proc. Natl. Acad. Sci. USA*, 89: 7840–7843 (1992).

Gagnerault et al., "Expression of Prolactin Receptors in Murine Lymphoid Cells in Normal and Autoimmune Situations", *J. Immunology*, 150: 5673–5681 (1993).
Gorodetsky et al., "Isolation and characterization of the Bos taurus β–casein gene", *Gene* 66: 87–96 (1988).
Hooghe et al., "Growth hormone and prolactin are paracrine growth and differentiation factors in the haemopoietic system", *Immunol. Today* 14: 212–214 (1993).
Koch et al., "The Common src Homoloogy Region 2 Domain of Cytoplasmic Signaling Proteins Is a Positive Effect of v–fps Tyrosine Kinase Function", *Mol. Cell. Biol.* 9: 4131–4140 (1989).
Lesueur et al., "Comparison of long and short forms of the prolactin receptor on prolactin–induced milk protein gene transcription", *Proc. Natl. Acad. Sci. USA* 88: 824–828 (1991).
Leung et al., "Growth hormone receptor and serum binding protein: purification, cloning and expression", *Nature* 330: 537–543 (1987).
Miyazaki et al., "The integrity of the conserved 'WS motif' common to IL–2 and other cytokine receptors in essential for ligand binding and signal transduction", *EMBO J.* 10: 3191–3197 (1991).
Murphy et al., "Differential Effects of Growth Hormone and Prolactin on Murine T Cell Development and Function", *J. Experi. Med.* 178: 231–236 (1993).
Robinson et al., "Prediction of neutral salt elution profiles for affinity chromatography", *Proc. Nat. Acad. Sci. USA* 78: 2287–2291 (1981).
Russell, "New aspects of prolactin and immunity: a lymphocyte–derived prolatin–like product and nuclear protein kinase C activation", *Trends Pharmacol. Sci.* 10: 40–44 (1989).
Schmitt–Ney et al., "β–Casein Gene Promoter Activity is Regulated by the Hormone–Mediated Relief of Transcriptional Repression and a Mammary–Gland–Specific Nuclear Factor", *Mol. Cell. Biol.* 11: 3745–3755 (1991).
Schmitt–Ney et al., "Developmental and environmental regulation of a mammary gland–specific nuclear factor essential for transcription of the gene encoding β–casein", *Proc. Natl. Acad. Sci. USA* 89: 3130–3134 (1992).
Shuai et al., "A Single Phosphotyrosine Residue of Stat91 Required for Gene Activation by Interferon–γ", *Science* 261: 1744–1746 (1993).

(List continued on next page.)

*Primary Examiner*—W. Gary Jones
*Assistant Examiner*—Dianne Rees
*Attorney, Agent, or Firm*—James Scott Elmer

[57] ABSTRACT

The present invention discloses isolated nucleic acids encoding MGF and recombinant proteins encoded thereby. In addition to being useful for the production of recombinant MGF, these nucleic acids are also useful as probes. In a further aspect of the invention, transfected host cells, particularly eukaryotic cells, containing and expressing such nucleic acids are provided. Furthermore, the present invention relates to methods for using such MGF proteins to identify and characterize compounds which affect the intracellular signal transduction of a lactogenic hormone.

5 Claims, No Drawings

OTHER PUBLICATIONS

Stahl et al., "Sequence similarity of phospholipase C with the non-catalytic region of src", *Nature* 332: 269–272 (1988).

Standke et al., "Mammary Gland Factor Activated by Prolactin in Mammary Epithelial Cells and Acute–Phase Response Factor Activated by Interleukin–6 in Liver Cells Share DNA Binding and Transactivation Potential", *Mol. Endocrinol.* 8(4): 469–477 (1994).

Vonderhaar et al., "Hormonal Regulation of Milk Protein Gene Expression", *Annu. Rev. Physiol.* 51: 641–652 (1989).

Wakao et al., "Mammary Gland–specific Nuclear Factor is Present in Lactating Rodent and Bovine Mammary Tissue and Composed of a Single Polypeptide of 89 kDa", *J. Biol. Chem.* 267: 16365–16370 (1992).

Wakao et al., "Mammary gland factor (MGF) is a novel member of the cytokine regulated transcription factor gene family and confers the prolactin response", EMBO J., 13: 2182–2191 (1994).

Wakao et al., "Molecular Cloning of MGF and its Identification as Prolactin Response Element Binding Protein", *J. Cell. Biochem. Suppl.* 0(18 Part A) 32, Abs. A418 (1994).

Witthuhn et al., "JAK2 Associates with the Erythropoietin Receptor and is Tyrosine Phosphorylated and Activated following Stimulation with Erythropoietin", *Cell* 74: 227–236 (1993).

Zhang et al., "Isolation and Characterization of Two Novel Rat Ovarian Lactogen Receptor cDNA Species", *Biochem. Biophys. res. Comm.* 168: 415–422 (1990).

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 2818 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 244..2625
        ( D ) OTHER INFORMATION: /product="mammary gland factor"

( x i ) SEQUENCE DESCRIPTION: SEQ ID NO:1:

```
GAATTCCGTT  GCTGTCGCGT  GGGATGCCAT  CGACCTGGAC  AATCCCCAGG  AGCCCCGGCC      60

GGAGCGAGCG  CCGGCCCCGT  CGCCGACCGC  CCGGCACGAC  CAGCCCTCCC  TCCTGAACAC     120

CCCAGCCACG  TGCCAGCGGT  TGCCGAGCCG  TCAGGGGAAA  CCTTCGGTGA  CCCTAGCTTT     180

GGGCTGGAAT  ATCCCCGCGT  TCCCAGAAAC  GGAGACTCGG  AGTTCGAAGC  AGGGTGAACG     240

GAC ATG GCG GGC TGG ATC CAG GCC CAG CAG CTG CAG GGA GAT GCC CTG            288
    Met Ala Gly Trp Ile Gln Ala Gln Gln Leu Gln Gly Asp Ala Leu
     1               5                  10                  15

CGC CAG ATG CAG GTG CTA TAC GGG CAG CAC TTC CCC ATC GAG GTC CGG           336
Arg Gln Met Gln Val Leu Tyr Gly Gln His Phe Pro Ile Glu Val Arg
                 20                  25                  30

CAT TAC TTG GCG CAG TGG ATT GAG AGC CAG CCG TGG GAT GCC ATC GAC           384
His Tyr Leu Ala Gln Trp Ile Glu Ser Gln Pro Trp Asp Ala Ile Asp
             35                  40                  45

CTG GAC ATT CCC CAG GAC CGG GCC CAG GTC ACC CAG CTC CTG GAG GGC           432
Leu Asp Ile Pro Gln Asp Arg Ala Gln Val Thr Gln Leu Leu Glu Gly
         50                  55                  60

CTG GTG CAG GAG TTG CAA AAG AAG GCA GAG CAC CAA GTC GGG GAA GAC           480
Leu Val Gln Glu Leu Gln Lys Lys Ala Glu His Gln Val Gly Glu Asp
     65                  70                  75

GGG TTC CTA CTG AAG ATC AAG CTG GGG CAC TAC GTC CAC GTC AGC TCC           528
Gly Phe Leu Leu Lys Ile Lys Leu Gly His Tyr Val His Val Ser Ser
 80                  85                  90                  95

AGA ACA CGT ACG ACC GCT GCC CCA TGG AGC TGG TTC CGC TGC ATT CGC           576
Arg Thr Arg Thr Thr Ala Ala Pro Trp Ser Trp Phe Arg Cys Ile Arg
                100                 105                 110
```

-continued

| | | | | | | | | | | | | | | | | |
|---|---|---|---|---|---|---|---|---|---|---|---|---|---|---|---|---|
| CAC | ATT | CTG | TAC | AAT | GAA | CAG | AGG | CTG | GTC | CGA | GAA | GCC | ACC | AAT | GGT | 624 |
| His | Ile | Leu | Tyr | Asn | Glu | Gln | Arg | Leu | Val | Arg | Glu | Ala | Thr | Asn | Gly | |
| | | | 115 | | | | 120 | | | | | 125 | | | | |
| AAT | TCT | TCT | GCT | GGG | ATC | CTG | GTT | GAT | GCC | ATG | TCC | CAG | AAA | CAC | CTT | 672 |
| Asn | Ser | Ser | Ala | Gly | Ile | Leu | Val | Asp | Ala | Met | Ser | Gln | Lys | His | Leu | |
| | | 130 | | | | 135 | | | | 140 | | | | | | |
| CAG | ATC | AAC | CAG | ACA | TTT | GAG | GAG | CTG | CGA | CTG | GTC | ACA | CAA | GAC | ACA | 720 |
| Gln | Ile | Asn | Gln | Thr | Phe | Glu | Glu | Leu | Arg | Leu | Val | Thr | Gln | Asp | Thr | |
| | 145 | | | | | 150 | | | | | 155 | | | | | |
| GAG | AAT | GAG | CTG | AAG | AAG | CTG | CAG | CAG | ACT | CAA | GAG | TAT | TTC | ATC | ATC | 768 |
| Glu | Asn | Glu | Leu | Lys | Lys | Leu | Gln | Gln | Thr | Gln | Glu | Tyr | Phe | Ile | Ile | |
| 160 | | | | | 165 | | | | | 170 | | | | | 175 | |
| CAG | TAT | CAG | GAG | AGC | CTG | AGG | ATC | CAG | GCT | CAG | TTT | GCC | CAG | CTG | GCC | 816 |
| Gln | Tyr | Gln | Glu | Ser | Leu | Arg | Ile | Gln | Ala | Gln | Phe | Ala | Gln | Leu | Ala | |
| | | | | 180 | | | | | 185 | | | | | 190 | | |
| CAG | CTG | AAC | CCC | CAG | GAG | CGA | CTG | AGC | CGG | GAG | ACG | GCC | CTC | CAG | CAG | 864 |
| Gln | Leu | Asn | Pro | Gln | Glu | Arg | Leu | Ser | Arg | Glu | Thr | Ala | Leu | Gln | Gln | |
| | | | 195 | | | | | 200 | | | | | 205 | | | |
| AAG | CAG | GTG | TCC | CTG | GAG | GCC | TGG | CTG | CAG | CGC | GAG | GCC | CAG | ACG | CTG | 912 |
| Lys | Gln | Val | Ser | Leu | Glu | Ala | Trp | Leu | Gln | Arg | Glu | Ala | Gln | Thr | Leu | |
| | | | 210 | | | | | 215 | | | | | 220 | | | |
| CAG | CAG | TAC | CGC | GTG | GAG | CTG | GCT | GAG | AAG | CAC | CAG | AAG | ACC | CTG | CAG | 960 |
| Gln | Gln | Tyr | Arg | Val | Glu | Leu | Ala | Glu | Lys | His | Gln | Lys | Thr | Leu | Gln | |
| | | 225 | | | | | 230 | | | | | 235 | | | | |
| CTG | CTG | CGG | AAG | CAG | CAG | ACC | ATC | ATC | CTG | GAT | GAC | GAG | CTG | AGC | CAG | 1008 |
| Leu | Leu | Arg | Lys | Gln | Gln | Thr | Ile | Ile | Leu | Asp | Asp | Glu | Leu | Ser | Gln | |
| 240 | | | | | 245 | | | | | 250 | | | | | 255 | |
| TGG | AAG | CGG | CGG | CAC | GAC | TGG | CGG | GGA | ATG | GAG | GCC | CCC | CCG | AGG | AGC | 1056 |
| Trp | Lys | Arg | Arg | His | Asp | Trp | Arg | Gly | Met | Glu | Ala | Pro | Pro | Arg | Ser | |
| | | | | 260 | | | | | 265 | | | | | 270 | | |
| CTG | GAT | GTG | CTA | CAG | TCC | TGG | TGT | GAG | AAG | TTG | GCG | GAG | ATC | ATC | TGG | 1104 |
| Leu | Asp | Val | Leu | Gln | Ser | Trp | Cys | Glu | Lys | Leu | Ala | Glu | Ile | Ile | Trp | |
| | | | 275 | | | | | 280 | | | | | 285 | | | |
| CAG | AAC | CGG | CAG | CAG | ATC | CGC | AGA | GCC | GAG | CAC | CTC | TGC | CAG | CAG | CTG | 1152 |
| Gln | Asn | Arg | Gln | Gln | Ile | Arg | Arg | Ala | Glu | His | Leu | Cys | Gln | Gln | Leu | |
| | | 290 | | | | | 295 | | | | | 300 | | | | |
| CCC | ATC | CCC | GGC | CCC | GTG | GAG | GAG | ATG | CTG | GCT | GAG | GTC | AAC | GCC | ACC | 1200 |
| Pro | Ile | Pro | Gly | Pro | Val | Glu | Glu | Met | Leu | Ala | Glu | Val | Asn | Ala | Thr | |
| | 305 | | | | | 310 | | | | | 315 | | | | | |
| ATC | ACG | GAC | ATC | ATC | TCA | GCC | CTG | GTG | ACC | AGC | ACA | TTC | ATC | ATC | GAG | 1248 |
| Ile | Thr | Asp | Ile | Ile | Ser | Ala | Leu | Val | Thr | Ser | Thr | Phe | Ile | Ile | Glu | |
| 320 | | | | | 325 | | | | | 330 | | | | | 335 | |
| AAG | CAG | CCC | CCT | CAG | GTC | CTG | AAG | ACC | CAG | ACC | AAG | TTC | GCG | GCC | ACC | 1296 |
| Lys | Gln | Pro | Pro | Gln | Val | Leu | Lys | Thr | Gln | Thr | Lys | Phe | Ala | Ala | Thr | |
| | | | | 340 | | | | | 345 | | | | | 350 | | |
| GTG | CGC | CTG | CTG | GTG | GGC | GGG | AAG | CTG | AAC | GTG | CAC | ATG | AAC | CCG | CCC | 1344 |
| Val | Arg | Leu | Leu | Val | Gly | Gly | Lys | Leu | Asn | Val | His | Met | Asn | Pro | Pro | |
| | | | 355 | | | | | 360 | | | | | 365 | | | |
| CAG | GTG | AAG | GCC | ACC | ATC | ATC | AGC | GAG | CAG | CAG | GCC | AAG | TCC | CTG | CTC | 1392 |
| Gln | Val | Lys | Ala | Thr | Ile | Ile | Ser | Glu | Gln | Gln | Ala | Lys | Ser | Leu | Leu | |
| | | | 370 | | | | | 375 | | | | | 380 | | | |
| AAG | AAC | GAG | AAC | ACC | CGC | AAT | GAG | TGC | AGC | GGG | GAG | ATC | CTG | AAC | AAC | 1440 |
| Lys | Asn | Glu | Asn | Thr | Arg | Asn | Glu | Cys | Ser | Gly | Glu | Ile | Leu | Asn | Asn | |
| | 385 | | | | | 390 | | | | | 395 | | | | | |
| TGC | TGT | GTG | ATG | GAG | TAC | CAC | CAG | CGC | ACA | GGC | ACC | CTC | AGC | GCC | CAC | 1488 |
| Cys | Cys | Val | Met | Glu | Tyr | His | Gln | Arg | Thr | Gly | Thr | Leu | Ser | Ala | His | |
| 400 | | | | | 405 | | | | | 410 | | | | | 415 | |
| TTC | AGG | AAC | ATG | TCC | CTC | AAG | AGG | ATC | AAG | CGA | GCT | GAC | CGG | CGA | GGC | 1536 |
| Phe | Arg | Asn | Met | Ser | Leu | Lys | Arg | Ile | Lys | Arg | Ala | Asp | Arg | Arg | Gly | |
| | | | | 420 | | | | | 425 | | | | | 430 | | |

```
GCA  GAG  TCT  GTG  ACA  GAA  GAG  AAG  TTC  ACG  GTC  CTG  TTT  GAG  TCT  CAA        1584
Ala  Glu  Ser  Val  Thr  Glu  Glu  Lys  Phe  Thr  Val  Leu  Phe  Glu  Ser  Gln
               435                      440                     445

TTC  AGT  GTT  GGC  AGC  AAT  GAG  CTT  GTG  TTC  CAG  GTG  AAG  ACC  CTG  TCC        1632
Phe  Ser  Val  Gly  Ser  Asn  Glu  Leu  Val  Phe  Gln  Val  Lys  Thr  Leu  Ser
               450                      455                     460

CTT  CCC  GTG  GTT  GTC  ATC  GTT  CAC  GGC  AGC  CAG  GAC  CAC  AAT  GCT  ACC        1680
Leu  Pro  Val  Val  Val  Ile  Val  His  Gly  Ser  Gln  Asp  His  Asn  Ala  Thr
     465                      470                     475

GCC  ACT  GTG  CTG  TGG  GAC  AAT  GCC  TTT  GCT  GAG  CCG  GGC  AGG  GTG  CCG        1728
Ala  Thr  Val  Leu  Trp  Asp  Asn  Ala  Phe  Ala  Glu  Pro  Gly  Arg  Val  Pro
480                      485                     490                      495

TTT  GCG  GTG  CCT  GAC  AAA  GTC  CTG  TGG  CCG  CAG  CTG  TGC  GAG  GCG  CTC        1776
Phe  Ala  Val  Pro  Asp  Lys  Val  Leu  Trp  Pro  Gln  Leu  Cys  Glu  Ala  Leu
                    500                     505                          510

AAC  ATG  AAA  TTC  AAG  GCC  GAG  GTG  CAG  AGC  AAC  CGG  GGC  CTG  ACC  AAG        1824
Asn  Met  Lys  Phe  Lys  Ala  Glu  Val  Gln  Ser  Asn  Arg  Gly  Leu  Thr  Lys
               515                      520                     525

GAG  AAC  CTG  TTG  TTT  CTG  GCG  CAG  AAG  CTG  TTC  AAC  AAC  AGC  AGC  AGC        1872
Glu  Asn  Leu  Leu  Phe  Leu  Ala  Gln  Lys  Leu  Phe  Asn  Asn  Ser  Ser  Ser
               530                      535                     540

CAC  CTC  GAG  GAC  TAC  AAC  GGC  ATG  TCT  GTG  TCC  TGG  TCC  CAG  TTC  AAC        1920
His  Leu  Glu  Asp  Tyr  Asn  Gly  Met  Ser  Val  Ser  Trp  Ser  Gln  Phe  Asn
     545                      550                     555

CGG  GAG  AAC  TTG  CCC  GGC  TGG  AAC  TAC  ACC  TTC  TGG  CAG  TGG  TTT  GAC        1968
Arg  Glu  Asn  Leu  Pro  Gly  Trp  Asn  Tyr  Thr  Phe  Trp  Gln  Trp  Phe  Asp
560                      565                     570                      575

GGG  GTC  ATG  GAG  GTG  CTG  AAG  AAA  CAT  CAC  AAG  CCC  CAC  TGG  AAT  GAC        2016
Gly  Val  Met  Glu  Val  Leu  Lys  Lys  His  His  Lys  Pro  His  Trp  Asn  Asp
               580                      585                     590

GGG  GCC  ATC  CTA  GGT  TTT  GTG  AAC  AAG  CAA  CAG  GCC  CAT  GAC  CTG  CTC        2064
Gly  Ala  Ile  Leu  Gly  Phe  Val  Asn  Lys  Gln  Gln  Ala  His  Asp  Leu  Leu
               595                      600                     605

ATC  AAC  AAG  CCC  GAC  GGT  ACC  TTC  TTG  TTG  CGC  TTT  AGC  GAC  TCA  GAA        2112
Ile  Asn  Lys  Pro  Asp  Gly  Thr  Phe  Leu  Leu  Arg  Phe  Ser  Asp  Ser  Glu
               610                      615                     620

ATT  GGG  GGC  ATC  ACC  ATT  GCC  TGG  AAG  TTT  GAC  TCT  CCT  GAC  CGT  AAC        2160
Ile  Gly  Gly  Ile  Thr  Ile  Ala  Trp  Lys  Phe  Asp  Ser  Pro  Asp  Arg  Asn
625                      630                     635

CTG  TGG  AAT  CTG  AAG  CCA  TTC  ACC  ACA  CGG  GAG  GGC  TCC  ATC  CGA  TCC        2208
Leu  Trp  Asn  Leu  Lys  Pro  Phe  Thr  Thr  Arg  Glu  Gly  Ser  Ile  Arg  Ser
640                      645                     650                      655

CTG  GCC  GAC  CGG  TTG  GGG  GAC  CTG  AAC  TAT  CTC  ATC  TAC  GTG  TTT  CCC        2256
Leu  Ala  Asp  Arg  Leu  Gly  Asp  Leu  Asn  Tyr  Leu  Ile  Tyr  Val  Phe  Pro
               660                      665                     670

GAC  CGG  CCC  AAG  GAT  GAG  GTC  TTC  TCC  AAG  TAC  TAC  ACT  CCT  GTG  CTT        2304
Asp  Arg  Pro  Lys  Asp  Glu  Val  Phe  Ser  Lys  Tyr  Tyr  Thr  Pro  Val  Leu
               675                      680                     685

GCC  AAA  GCA  GTG  GAC  GGA  TAC  GTG  AAG  CCG  CAG  ATC  AAA  CAA  GTG  GTC        2352
Ala  Lys  Ala  Val  Asp  Gly  Tyr  Val  Lys  Pro  Gln  Ile  Lys  Gln  Val  Val
               690                      695                     700

CCT  GAG  TTT  GTG  AGC  GCC  TCT  GCA  GAC  TCT  GCT  GGA  AGC  AGC  GCC  ACC        2400
Pro  Glu  Phe  Val  Ser  Ala  Ser  Ala  Asp  Ser  Ala  Gly  Ser  Ser  Ala  Thr
     705                      710                     715

TAC  ATG  GAC  CAG  GCT  CCC  TCC  CCA  GCC  GTG  TGC  CCC  CAG  CCT  CAC  TAT        2448
Tyr  Met  Asp  Gln  Ala  Pro  Ser  Pro  Ala  Val  Cys  Pro  Gln  Pro  His  Tyr
720                      725                     730                      735

AAC  ATG  TAC  CCA  CAG  AAC  CCT  GAC  CCG  GTG  CTC  GAC  CAG  GAT  GGA  GAA        2496
Asn  Met  Tyr  Pro  Gln  Asn  Pro  Asp  Pro  Val  Leu  Asp  Gln  Asp  Gly  Glu
               740                      745                     750
```

| | | | | | | | | | | | | | | | | |
|---|---|---|---|---|---|---|---|---|---|---|---|---|---|---|---|---|
| TTT | GAC | CTG | GAC | GAG | ACC | ATG | GAT | GTG | GCC | CGG | CAC | GTG | GAA | GAA | CTC | 2544 |
| Phe | Asp | Leu | Asp | Glu | Thr | Met | Asp | Val | Ala | Arg | His | Val | Glu | Glu | Leu | |
| | | | 755 | | | | 760 | | | | | 765 | | | | |
| CTC | CGC | CGC | CCC | AAT | GGA | CAG | TCT | GGA | CCC | CTC | TCT | CCC | CCG | CCC | GCT | 2592 |
| Leu | Arg | Arg | Pro | Asn | Gly | Gln | Ser | Gly | Pro | Leu | Ser | Pro | Pro | Pro | Ala | |
| | | 770 | | | | 775 | | | | | 780 | | | | | |
| GGT | CTC | TTT | ACT | CCT | GCC | AGA | GGC | TCG | CTC | TCC | TGAATGTTTG | | TTCGAACACT | | | 2645 |
| Gly | Leu | Phe | Thr | Pro | Ala | Arg | Gly | Ser | Leu | Ser | | | | | | |
| | | 785 | | | | 790 | | | | | | | | | | |

| | | | | |
|---|---|---|---|---|
| GCACTCCTCT | GTGGGAACAA | TCCCCAGTGT | GCAGGGTCCT | ATTCATTGTG ATTTTGTGTT | 2705 |
| TGTATCTCTG | TGCATACTGA | TGCCTTTGCA | GGCAGCCCAC | GTACACGTGT AGACGTGCAC | 2765 |
| GCGCATTTGT | GTACGAGGTG | TGCCCACTTC | GCCTCCGCAG | TCCTAGGTGT GCG | 2818 |

( 2 ) INFORMATION FOR SEQ ID NO:2:

( i ) SEQUENCE CHARACTERISTICS:
        ( A ) LENGTH: 794 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Gly Trp Ile Gln Ala Gln Gln Leu Gln Gly Asp Ala Leu Arg
 1               5                  10                  15

Gln Met Gln Val Leu Tyr Gly Gln His Phe Pro Ile Glu Val Arg His
            20                  25                  30

Tyr Leu Ala Gln Trp Ile Glu Ser Gln Pro Trp Asp Ala Ile Asp Leu
        35                  40                  45

Asp Ile Pro Gln Asp Arg Ala Gln Val Thr Gln Leu Leu Glu Gly Leu
    50                  55                  60

Val Gln Glu Leu Gln Lys Lys Ala Glu His Gln Val Gly Glu Asp Gly
65                  70                  75                  80

Phe Leu Leu Lys Ile Lys Leu Gly His Tyr Val His Val Ser Ser Arg
                85                  90                  95

Thr Arg Thr Thr Ala Ala Pro Trp Ser Trp Phe Arg Cys Ile Arg His
            100                 105                 110

Ile Leu Tyr Asn Glu Gln Arg Leu Val Arg Glu Ala Thr Asn Gly Asn
        115                 120                 125

Ser Ser Ala Gly Ile Leu Val Asp Ala Met Ser Gln Lys His Leu Gln
    130                 135                 140

Ile Asn Gln Thr Phe Glu Glu Leu Arg Leu Val Thr Gln Asp Thr Glu
145                 150                 155                 160

Asn Glu Leu Lys Lys Leu Gln Gln Thr Gln Glu Tyr Phe Ile Ile Gln
                165                 170                 175

Tyr Gln Glu Ser Leu Arg Ile Gln Ala Gln Phe Ala Gln Leu Ala Gln
            180                 185                 190

Leu Asn Pro Gln Glu Arg Leu Ser Arg Glu Thr Ala Leu Gln Gln Lys
        195                 200                 205

Gln Val Ser Leu Glu Ala Trp Leu Gln Arg Glu Ala Gln Thr Leu Gln
    210                 215                 220

Gln Tyr Arg Val Glu Leu Ala Glu Lys His Gln Lys Thr Leu Gln Leu
225                 230                 235                 240

Leu Arg Lys Gln Gln Thr Ile Ile Leu Asp Asp Glu Leu Ser Gln Trp
                245                 250                 255

Lys Arg Arg His Asp Trp Arg Gly Met Glu Ala Pro Pro Arg Ser Leu
            260                 265                 270
```

```
Asp Val Leu Gln Ser Trp Cys Glu Lys Leu Ala Glu Ile Trp Gln
        275                 280                 285

Asn Arg Gln Gln Ile Arg Arg Ala Glu His Leu Cys Gln Gln Leu Pro
    290                 295                 300

Ile Pro Gly Pro Val Glu Glu Met Leu Ala Glu Val Asn Ala Thr Ile
305                 310                 315                 320

Thr Asp Ile Ile Ser Ala Leu Val Thr Ser Thr Phe Ile Ile Glu Lys
                325                 330                 335

Gln Pro Pro Gln Val Leu Lys Thr Gln Thr Lys Phe Ala Ala Thr Val
            340                 345                 350

Arg Leu Leu Val Gly Gly Lys Leu Asn Val His Met Asn Pro Pro Gln
        355                 360                 365

Val Lys Ala Thr Ile Ile Ser Glu Gln Gln Ala Lys Ser Leu Leu Lys
    370                 375                 380

Asn Glu Asn Thr Arg Asn Glu Cys Ser Gly Glu Ile Leu Asn Asn Cys
385                 390                 395                 400

Cys Val Met Glu Tyr His Gln Arg Thr Gly Thr Leu Ser Ala His Phe
                405                 410                 415

Arg Asn Met Ser Leu Lys Arg Ile Lys Arg Ala Asp Arg Arg Gly Ala
            420                 425                 430

Glu Ser Val Thr Glu Glu Lys Phe Thr Val Leu Phe Glu Ser Gln Phe
        435                 440                 445

Ser Val Gly Ser Asn Glu Leu Val Phe Gln Val Lys Thr Leu Ser Leu
    450                 455                 460

Pro Val Val Val Ile Val His Gly Ser Gln Asp His Asn Ala Thr Ala
465                 470                 475                 480

Thr Val Leu Trp Asp Asn Ala Phe Ala Glu Pro Gly Arg Val Pro Phe
                485                 490                 495

Ala Val Pro Asp Lys Val Leu Trp Pro Gln Leu Cys Glu Ala Leu Asn
            500                 505                 510

Met Lys Phe Lys Ala Glu Val Gln Ser Asn Arg Gly Leu Thr Lys Glu
        515                 520                 525

Asn Leu Leu Phe Leu Ala Gln Lys Leu Phe Asn Asn Ser Ser Ser His
    530                 535                 540

Leu Glu Asp Tyr Asn Gly Met Ser Val Ser Trp Ser Gln Phe Asn Arg
545                 550                 555                 560

Glu Asn Leu Pro Gly Trp Asn Tyr Thr Phe Trp Gln Trp Phe Asp Gly
                565                 570                 575

Val Met Glu Val Leu Lys Lys His His Lys Pro His Trp Asn Asp Gly
            580                 585                 590

Ala Ile Leu Gly Phe Val Asn Lys Gln Gln Ala His Asp Leu Leu Ile
        595                 600                 605

Asn Lys Pro Asp Gly Thr Phe Leu Leu Arg Phe Ser Asp Ser Glu Ile
    610                 615                 620

Gly Gly Ile Thr Ile Ala Trp Lys Phe Asp Ser Pro Asp Arg Asn Leu
625                 630                 635                 640

Trp Asn Leu Lys Pro Phe Thr Thr Arg Glu Gly Ser Ile Arg Ser Leu
                645                 650                 655

Ala Asp Arg Leu Gly Asp Leu Asn Tyr Leu Ile Tyr Val Phe Pro Asp
            660                 665                 670

Arg Pro Lys Asp Glu Val Phe Ser Lys Tyr Tyr Thr Pro Val Leu Ala
        675                 680                 685

Lys Ala Val Asp Gly Tyr Val Lys Pro Gln Ile Lys Gln Val Val Pro
```

|  |  |  |  |  |  |  |  |  |  |  |  |  |  |  |
|---|---|---|---|---|---|---|---|---|---|---|---|---|---|---|
|  | 690 |  |  |  | 695 |  |  |  |  | 700 |  |  |  |  |
| Glu | Phe | Val | Ser | Ala | Ser | Ala | Asp | Ser | Ala | Gly | Ser | Ser | Ala | Thr | Tyr |
| 705 |  |  |  |  | 710 |  |  |  | 715 |  |  |  |  |  | 720 |
| Met | Asp | Gln | Ala | Pro | Ser | Pro | Ala | Val | Cys | Pro | Gln | Pro | His | Tyr | Asn |
|  |  |  |  | 725 |  |  |  |  | 730 |  |  |  |  | 735 |  |
| Met | Tyr | Pro | Gln | Asn | Pro | Asp | Pro | Val | Leu | Asp | Gln | Asp | Gly | Glu | Phe |
|  |  |  | 740 |  |  |  |  | 745 |  |  |  |  | 750 |  |  |
| Asp | Leu | Asp | Glu | Thr | Met | Asp | Val | Ala | Arg | His | Val | Glu | Glu | Leu | Leu |
|  |  | 755 |  |  |  |  | 760 |  |  |  |  |  | 765 |  |  |
| Arg | Arg | Pro | Asn | Gly | Gln | Ser | Gly | Pro | Leu | Ser | Pro | Pro | Pro | Ala | Gly |
|  | 770 |  |  |  |  | 775 |  |  |  |  | 780 |  |  |  |  |
| Leu | Phe | Thr | Pro | Ala | Arg | Gly | Ser | Leu | Ser |
| 785 |  |  |  |  | 790 |  |  |  |  |

( 2 ) INFORMATION FOR SEQ ID NO:3:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="MGF binding site in
            b-casein gene"

( i i i ) HYPOTHETICAL: NO ( x i ) SEQUENCE DESCRIPTION: SEQ ID NO:3:

ACTTCTTGGA ATT                                      13

( 2 ) INFORMATION FOR SEQ ID NO:4:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:4:

Val  Asp  Gly  Tyr  Val  Lys  Pro
    1                    5

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( x i ) SEQUENCE DESCRIPTION: SEQ ID NO:5:

Gly  Thr  Phe  Leu  Leu  Arg  Phe  Ser  Xaa  Ser
    1                    5                    10

( 2 ) INFORMATION FOR SEQ ID NO:6:

( i ) SEQUENCE CHARACTERISTICS:
        ( A ) LENGTH: 7 amino acids (B) TYPE: amino acid
(C) STRANDEDNESS: single
(D) TOPOLOGY: linear (ii) MOLECULE TYPE: peptide (iii) HYPOTHETICAL: NO (xi) SEQUENCE DESCRIPTION: SEQ ID NO:6:

Arg Leu Gly Asp Leu Asn Tyr
1               5

(2) INFORMATION FOR SEQ ID NO:7:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: /desc ="MGF binding sequence from rat b- casein"

(iii) HYPOTHETICAL: NO (xi) SEQUENCE DESCRIPTION: SEQ ID NO:7:

GGACTTCTTG GAATTAAGGG A          21

(2) INFORMATION FOR SEQ ID NO:8:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: /desc ="MGF binding sequence from bovine b- casein"

(iii) HYPOTHETICAL: NO (xi) SEQUENCE DESCRIPTION: SEQ ID NO:8:

AGATTTCTAG GAATTCAATC C          21

(2) INFORMATION FOR SEQ ID NO:9:

(i) SEQUENCE CHARACTERISTICS:
(A) LENGTH: 14 amino acids
(B) TYPE: amino acid
(C) STRANDEDNESS: single
(D) TOPOLOGY: linear (ii) MOLECULE TYPE: peptide (iii) HYPOTHETICAL: NO (xi) SEQUENCE DESCRIPTION: SEQ ID NO:9:

Gln Gln Thr Ile Ile Leu Asp Asp Glu Leu Ile Gln Trp Lys
1               5                   10

(2) INFORMATION FOR SEQ ID NO:10:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide ( i i i ) HYPOTHETICAL: NO ( x i ) SEQUENCE DESCRIPTION: SEQ ID NO:10:

Tyr Val Lys Pro Gln Ile
1               5

( 2 ) INFORMATION FOR SEQ ID NO:11:

( i ) SEQUENCE CHARACTERISTICS:
      ( A ) LENGTH: 42 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc ="oligonucleotide used to
          screen cDNA library"

( i i i ) HYPOTHETICAL: NO ( i x ) FEATURE:
      ( A ) NAME/KEY: modified_base
      ( B ) LOCATION: 12
      ( D ) OTHER INFORMATION: /mod_base=i ( i x ) FEATURE:
      ( A ) NAME/KEY: modified_base
      ( B ) LOCATION: 18
      ( D ) OTHER INFORMATION: /mod_base=i ( i x ) FEATURE:
      ( A ) NAME/KEY: modified_base
      ( B ) LOCATION: 21
      ( D ) OTHER INFORMATION: /mod_base=i ( i x ) FEATURE:
      ( A ) NAME/KEY: modified_base
      ( B ) LOCATION: 24
      ( D ) OTHER INFORMATION: /mod_base=i ( x i ) SEQUENCE DESCRIPTION: SEQ ID NO:11:

TTCCACTGGA TNAGCTCNTC NTCNAGGATG ATGGTCTGCT GT    42

( 2 ) INFORMATION FOR SEQ ID NO:12:

( i ) SEQUENCE CHARACTERISTICS:
      ( A ) LENGTH: 32 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc ="oligonucleotide used to
          screen cDNA library"

( i i i ) HYPOTHETICAL: NO ( i x ) FEATURE:
      ( A ) NAME/KEY: modified_base
      ( B ) LOCATION: 6
      ( D ) OTHER INFORMATION: /mod_base=i ( i x ) FEATURE:
      ( A ) NAME/KEY: modified_base
      ( B ) LOCATION: 15
      ( D ) OTHER INFORMATION: /mod_base=i ( i x ) FEATURE:
      ( A ) NAME/KEY: modified_base
      ( B ) LOCATION: 18
      ( D ) OTHER INFORMATION: /mod_base=i ( i x ) FEATURE:
      ( A ) NAME/KEY: modified_base
      ( B ) LOCATION: 27
      ( D ) OTHER INFORMATION: /mod_base=i ( x i ) SEQUENCE DESCRIPTION: SEQ ID NO:12:

ATCTGNGGYT TCACNCCNCC GTCCACNGCY TT  32

CYTOKINE REGULATED TRANSCRIPTION FACTOR

Prolactin exerts pleiotropic biological effects in vertebrates and is involved in the regulation of reproduction, cell growth, lactation, steroidogenesis, maternal behaviour, osmoregulation, metabolism and the immune response (Russell, D. H. (1989) *Trends Pharmacol. Sci.*, 10: 40–44; Kelly et al., (1991) *Endocrine Rev.* 12:235–251.). Prolactin is best known for its role in the development of the mammary gland and its control of lactation. It promotes milk protein gene expression by regulating the transcription and the stability of mRNA (Vonderhaar and Ziska, (1989) *Ann. Rev. Physiol.*, 51:641–652). The role of prolactin in the immune system has also been extensively studied (Gagnerault et al., (1993) *J. Immunology*, 150:5673–5681; Murphy et al., (1993) *J. Experi. Med.*, 178:231–236.; Hooghe et al., (1993) *Immunol. Today*, 14:212–214).

Prolactin is a peptide hormone produced in the anterior pituitary and a member of the growth hormone/prolactin/placental lactogen gene family. It exerts its function via the prolactin receptor (PRLR), a member of the cytokine/hematopoietic growth factor receptor family. Growth hormone (GH) (Leung et al., (1987) *Nature*. 330:537–543), erythropoietin (EPO) (D'Andrea et al., (1989 *Mol. Cell. Biol.*, 11:1980–1987), IL-2 (Hatakeyama et al., (1989) *Science*. 244:551–556), IL-3 (Itoh et al., (1990) *Science*. 247:324–237), IL-4 (Mosley et al., (1989) *Cell* 59:335–348), IL-5 (Takaki et al., (1990) *EMBO J.*, 9:4367–4374), IL-6 (Yamasaki et al., (1988) *Science* 241:825–828), IL-7 (Goodwin et al., (1990) *Cell* 60:941–951), granulocyte-macrophage colony-stimulating factor (GM-CSF) (Gearing et al., (1989) *EMBO J.* 8:3667–3676), granulocyte colony-stimulating factor (G-CSF) (Fukunaga et al., (1990) *Cell* 61:341–350), leukaemia inhibiting factor (LIF) (Gearing et al., (1991) *EMBO J.*, 10:2839–2848) and ciliary neurotrophic factor (CNTF) (Davis et al., (1991) *Science* 253:59–63) act via receptors belonging to this family. The extracellular domains of these receptors share structural similarities (Cosman et al., (1990) *Trends. Biochem. Sci.*, 15:265–270) and contain the protein motif W-S-X-W-S. They also contain four paired cysteine residues possibly important for ligand binding (Bazan, (1990) *Proc. Natl. Acad. Sci.*, 87: 6934–6938; Miyazaki et al., (1991) *EMBO J.*, 10:3191–3197; Kelly et al., supra.). Among the ligands, only growth hormone and prolactin are structurally related.

Prolactin triggers cellular responses by binding to a cell surface receptor. PRLR have been cloned from different species (Boutin et al., 1988; 1989; Edery et al., (1989) *Proc. Natl. Acad. Sci.*, 86: 2112–2116); Davis et al., (1989) *Mol. Endocrinol.*, 3:674–680); Zhang et al., (1990) *Biochem. Biophys. Res. Comm.*, 168:415–422.); Shirota et al., (1990) *Mol. Endocrinol.*, 4:1136–1143). There are isoforms of PRLR, a short form with 57 amino acids of intracellular domain, and a longer form with 358 amino acids. Both forms have identical extracellular and transmembrane domains and can be expressed in the same tissue (Shirota et al., supra.). The comparison of the biological function as signal transducers has shown that the isoforms are distinguishable (Lesueur et al., (1991) *Proc. Natl. Acad. Sci.*, 88:824–828). A third, intermediate receptor form was found in Nb2, pre-T rat lymphoma cells. Nb2 cells require prolactin for growth. This PRLR is lacking 198 amino acids in its cytoplasmic domain when compared to the long form (Ali et al., (1991) *J. Biol. Chem.*, 266:20110–20117).

In contrast to PDGF and EGF receptors, which contain intrinsic tyrosine kinase activities (Schlessinger and Ullrich, (1993) *Neuron* 9:383–391), members of cytokine/hematopoietic growth factor receptor family do not have such an enzymatic activity. Nevertheless, protein tyrosine phosphorylation has been implicated in the signalling cascades of these receptors. The tyrosine specific protein kinase JAK2 is associated with the EPO receptor and the GH receptor and also is activated by prolactin (Witthuhn et al., (1993) *Cell*, 74:227–236; Argetsinger et al., (1993) *Cell*, 74; Rui et al., (1994) *J. Biol. Chem.* in press).

The mechanism by which gene transcription is regulated by prolactin has been most extensively studied in mammary epithelial cells. A lactogenic hormone response element within the proximal 335 bp of the rat β-casein gene promoter has been found (Doppler et al., (1989) *Proc. Natl. Acad. Sci.*, 86:104–108). Prolactin and glucocorticoids synergistically induce β-casein gene transcription. The binding site of a transcription factor (mammary gland factor, MGF) was identified in the β-casein gene promoter (Schmitt-Ney et al., (1991) *Mol. Cell. Bid.*, 11:3745–3755). This sequence, 5'-ACTTCTTGGAATT-3' (SEQ ID NO: 3) is highly conserved in the promoter region of the casein genes (Yoshimura and Oka, (1989) *Gene* 78:267–275; Wakao et al., (1992) *J. Biol. Chem.*, 267:16365–16370). MGF binding is indispensable for β-casein gene promoter activity. MGF is a transducer of lactogenic hormone and environmental signals. Its activity is highly regulated during gestation, lactation, and post-lactation. Little DNA binding activity is detected at early stages of pregnancy. Its activity increases towards the end of pregnancy. At the end of gestation, high levels of MGF activity are observed and maintained during the lactation period. At post-lactation, very little activity is detected. During lactation the level of MGF activity is controlled in part through signals induced by the suckling of the pups (Schmitt-Ney et al., supra.), most likely by the level of circulating prolactin.

The present invention discloses isolated nucleic acids encoding MGF and recombinant proteins encoded thereby. In addition to being useful for the production of recombinant MGF, these nucleic acids are also useful as probes, thus readily enabling those skilled in the art to identify and/or isolate nucleic acids encoding an MGF protein. The recombinant DNAs, RNAs and proteins of the invention may be useful in ways that the DNAs, RNAs and proteins as they naturally occur are not, such as identification of compounds or drugs selectively modulating the biological activity of MGF or a protein capable of interacting with MGF, particularly a protein capable of activating MGF. Exemplary proteins capable of activating MGF are e.g. cytokines, such as lactogenic hormone.

As used hereinbefore or hereinafter, the term "isolated" is intended to refer to a molecule of the invention in an enriched or, preferably, pure form obtainable from a natural source or by means of genetic engineering.

The isolated DNAs, RNAs and proteins of the invention may be useful in ways that the DNAs, RNAs and proteins as they naturally occur are not, such as identification of compounds selectively modulating the activity of MGF.

Isolated MGF nucleic acid includes nucleic acid that is free from at least one contaminant nucleic acid with which it is ordinarily associated in the natural source of MGF nucleic acid. Isolated nucleic acid thus is present in other than in the form or setting in which it is found in nature. However, isolated MGF encoding nucleic acid includes MGF nucleic acid in ordinarily MGF-expressing cells where the nucleic acid is in a chromosomal location different from that of natural cells or is otherwise flanked by a different DNA sequence than that found in nature.

In a still further aspect of the invention, transformed host cells, particularly eukaryotic cells, containing and expressing such nucleic acids are provided. In another embodiment of the present invention, there are provided nucleic acid probes comprising MGF-selective portions of the above-described nucleic acids.

Furthermore, the present invention relates to methods for using such MGF proteins to identify and characterize compounds which affect the intracellular signal transduction of a lactogenic hormone, e.g. agonists, antagonists and modulators of the prolactin receptor, the protein kinase JAK 2 and/or MGF.

In another aspect, the present invention relates to methods for using such MGF proteins to identify and characterize compounds which affect the intracellular signal transduction of a cytokine, e.g. agonists, antagonists and modulators of a cytokine, particularly a cytokine mentioned below, or a receptor of such a cytokine, and/or MGF.

The activation of MGF is not restricted to prolactin response. Erythropoietin (EPO) and growth hormone (GH) stimulate the DNA binding activity of MGF, e.g. in COS cells transfected with vectors encoding EPO receptor and MGF or vectors encoding GH receptor and MGF. Activation of DNA binding by prolactin, EPO and GH requires phosphorylation of tyrosine residue 694 of MGF. The transcriptional induction of a β-casein promoter luciferase construct in transiently transfected COS cells is specific for the prolactin activation of MGF and not observed in EPO and GH treated cells. In a human hematopoetic cell line, e.g. the UT7 or U937 human hematopoetic cell lines, EPO and granulocyte-macrophage stimulating factor (GM-CSF) activate the DNA binding activity of a factor closely related to MGF with respect to its immunological reactivity, its DNA binding specificity and its molecular weight. MGF regulate physiological processes in mammary epithelial cells as well as in hematopoetic cells. Its DNA binding activity and transactivation potential are differentially regulated in a cytokine and promoter specific manner.

MGF plays a role in the transduction of signals generated by different cytokines, e.g IL-3 and IL- 5. The GAS elements found in the FcγRI and IRF-1 gene promoters are efficient competitors for factor binding. MGF may also be referred to as MGF-Stat5.

In accordance with the present invention, there are provided isolated nucleic acids, e.g. DNAs or RNAs, encoding mammalian MGF. Exemplary nucleic acids encoding MGF are represented in SEQ ID NO: 1. Especially preferred sequences encoding MGF are those having substantially the same nucleotide sequence as the coding sequences in SEQ ID NO: 1, with the nucleic acids having the same sequence as the coding sequence in SEQ ID NO: 1 being most preferred. Exemplary nucleic acids can alternatively be characterized as those nucleotide sequences which encode an MGF protein and hybridize to the DNA sequence set forth in SEQ ID NO: 1, or a selected portion or fragment of said DNA sequence. A preferred fragment is represented e.g. by a nucleic acid which has the same nucleotide sequence as the coding sequence set forth in SEQ ID NO: 1, or a nucleic acid coding for a peptide having an amino acid sequence as underlined. Further exemplary oligonucleotides useful for hybridisation are those employed in the Examples for the isolation of the cDNA clones encoding MGF. Hybridization is effected under such conditions under which polynucleic acids hybrids are stable. Such conditions are evident to those of ordinary skill in the art.

As used herein, nucleotide sequences which are substantially the same share at least about 90% identity. However, in the case of splice variants having e.g. an additional exon sequence homology may be lower. Preferred are such sequences encoding MGF which hybridize under high-stringency conditions to an above-mentioned nucleic acid.

DNA encoding MGF may be isolated by screening suitable cDNA or genomic libraries under suitable hybridization conditions with DNA disclosed herein including oligonucleotides derived from the sequence set forth in SEQ ID NO: 1. Suitable libraries can be prepared e.g. from tissue samples, cell lines and the like. For example, the library can be screened with a portion of DNA including substantially the entire MGF-encoding sequence, or the library may be screened with a suitable oligonucleotide probe based on a portion of the DNA.

Given the guidance provided herein, the nucleic acids of the invention are obtainable according to methods well known in the art. For example, a DNA of the invention is obtainable by chemical sythesis, using polymerase chain reaction (PCR) or by screening a genomic library or a suitable cDNA library prepared from a source believed to possess MGF and to express it at a detectable level.

As used herein, a probe is e.g. a single-stranded DNA or RNA that has a sequence of nucleotides that includes at least about 20 contiguous bases that are the same as (or the complement of) any 20 or more contiguous bases set forth in FIG. 1. Preferred regions from which to construct probes include 5' and/or 3' coding sequences, sequences predicted to encode ligand binding sites, and the like.

Either the full-length DNA clones, e.g. cDNA clones, or fragments thereof can be used as probes. Preferably, nucleic acid probes of the invention are labeled with suitable label means for ready detection.

In order to detect any abnormality of endogenous MGF, genetic screening may be carried out using the nucleotide sequences of the invention as hybridization probes. Also, based on the nucleic acid sequences provided herein antisense-type therapeutic agents may be designed.

It is envisaged that the nucleic acid of the invention can be readily modified by nucleotide substitution, nucleotide deletion, nucleotide insertion or inversion of a nucleotide stretch, and any combination thereof. Such mutants can be used e.g. to produce an MGF mutein (mutant protein) that has an amino acid sequence differing from the MGF sequences as found in nature. Mutagenesis may be predetermined (site-specific) or random. A mutation which is not a silent mutation must not place sequences out of reading frames and preferably will not create complementary regions that could hybridize to produce secondary mRNA structure such as loops or hairpins.

In accordance with another embodiment of the present invention, there is provided a method for identifying DNA encoding human MGF, said method comprising contacting human DNA with a nucleic acid probe as described above, wherein said contacting is carried out under hybridization conditions, and identifying DNA(s) which hybridize to said probe.

After screening the library, positive clones are identified by detecting a hybridization signal; the identified clones are characterized by restriction enzyme mapping and/or DNA sequence analysis, and then examined, e.g. by comparison with the sequence set forth herein, to ascertain whether they include DNA encoding a complete MGF (i.e., if they include translation initiation and termination codons). If the selected clones are incomplete, they may be used to rescreen the same or a different library to obtain overlapping clones. If the library is genomic, then the overlapping clones may include exons and introns. If the library is a cDNA Library, then the overlapping clones will include an open reading frame. In both instances, complete clones may be identified by comparison with the DNA and deduced amino acid sequences provided herein.

The above-described nucleotide sequences can be incorporated into vectors for further manipulation. As used herein, vector (or plasmid) refers to discrete elements that are used to introduce heterologous DNA into cells for either expression or replication thereof. Selection and use of such vehicles are well within the skill of the artisan. An expression vector includes vectors capable of expressing DNAs that are operatively linked with regulatory sequences, such as promoter regions, that are capable of expression of such DNA fragments. Thus, an expression vector refers to a recombinant DNA or RNA construct, such as a plasmid, a phage, recombinant virus or other vector, that upon introduction into an appropriate host cell, results in expression of the cloned DNA. Appropriate expression vectors are well known to those with ordinary skill in the art and include those that are replicable in eukaryotic and/or prokaryotic cells and those that remain episomal or those which integrate into the host cell genome. For example, DNAs encoding MGF may be inserted into the pXM eukaryotic expression vector.

Construction of vectors according to the invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing MGF expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridization, using an appropriately labelled probe based on a sequence provided herein. Suitable methods include those described in detail in the Examples. Those skilled in the art will readily envisage how these methods may be modified, if desired.

In accordance with another embodiment of the present invention, there are provided cells containing the above-described polynucleic acids (i.e., DNA or mRNA). Such host cell as bacterial, yeast and mammalian cells can be used for replicating DNA and producing MGF. Suitable methods for constructing expression vectors, preparing in vitro transcripts, transfecting DNA into mammalian cells, and performing analyses for assessing MGF expression and function are known to those skilled in the art, e.g. the particular methods employed herein. These methods are described in detail in the Examples.

Those skilled in the art will readily envisage how these methods may be modified, if desired. Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g. Sambrook et al. (1989) Molecular Cloning: A Laboratory Manual, Second Edition, Cold Spring Harbor Laboratory Press). Heterologous DNA may be introduced into host cells by any method known in the art, such as transfection with a vector encoding a heterologous DNA by the calcium phosphate precipitation technique. Transfected cells can then be cultured under conditions whereby MGF encoded by the DNA is expressed. Preferred cells include mammalian cells, e.g. COS cells or CHO cells, yeast cells, bacterial cells, e.g. E. coli, and the like.

While the DNA provided herein may be expressed in any eukaryotic cell, mammalian expression systems, including commercially available systems and other systems known to those of skill in the art which express the prolactin receptor (either endogenously or recombinantly), are preferred for expression of DNA encoding functional MGF.

In preferred embodiments, MGF-encoding DNA is ligated into a vector, and introduced into suitable host cells to produce transformed cell lines that express MGF. The resulting cell lines can then be produced in quantity for reproducible quantitative analysis of the effects of potential drugs, e.g. on MGF function. The transfected mammalian cells may then be used in the methods of drug screening provided herein. Preferred cells are those that express little, if any, endogenous MGF, and can be transiently or stably transfected and also express invention DNA and RNA. Presently most preferred are cells that can form recombinant or heterologous MGF encoded by the heterologous DNA. Such cells may be identified empirically or selected from among those known to be readily transfected.

DNA may be stably incorporated into cells or may be transiently expressed using methods known in the art. Stably transfected mammalian cells may be prepared by transfecting cells with an expression vector having a selectable marker gene, and growing the transfected cells under conditions selective for cells expressing the marker gene. To prepare transient transfectants, mammalian cells are transfected with a reporter gene to monitor transfection efficiency.

To produce such stably or transiently transfected cells, the cells should be transfected with a sufficient amount of MGF-encoding nucleic acid to form MGF. The precise amounts of DNA encoding MGF may be empirically determined and optimized for a particular cell and assay.

Those of skill in the art can readily identify a variety of assays which can be used to detect the expression of functional MGF. Reference is made to the assays employed in the Examples.

Being a promoter-specific transcription factor (β-casein promoter) MGF is a target for therapeutical intervention e.g. by means of a chemical entity affecting the factor's capability of binding to the DNA. The screening for such chemical entities may be performed e.g. by means of a cell-based assay, an in vitro assay for MGF function and/or rational drug design.

Cell-based assays for screening can be designed e.g. by constructing cell lines in which the expression of a reporter protein, i.e. an easily assayable protein, is dependent on MGF. Such an assay enables the detection of compounds that directly antagonize MGF, or compounds that inhibit other cellular functions required for the activity of MGF.

An in vitro assay for MGF requires that it may be produced in large amounts in a functional form using recombinant DNA methods. An assay is then designed to measure a functional property of the MGF protein, e.g. DNA binding. An exemplary in vitro assay is the bandshift assay used in the Examples.

It has been found that MGF is expressed e.g. in mammary gland, ovary, thymus spleen, kidney, lung muscle, the adrenal gland, B cells and T cells. The present invention provides methods for affecting the cellular signal transduction emanating from the prolactin receptor. For example, the present invention enables to exogenously affect the function of B cells, T-cells or mammary epithelial cells.

In accordance with still another embodiment of the invention, there is provided a method for identifying compounds which modulate the activity of MGF, said method comprising exposing cells containing heterologous DNA encoding MGF, wherein said cells produce functional MGF, to at least one compound or signal whose ability to modulate the activity of said MGF is sought to be determined, and thereafter monitoring said cells for changes caused by said modulation. Such an assay enables the identification of agonists, antagonists and allosteric modulators of MGF.

Recombinant MGF producing mammalian cells can be contacted with a test compound, and the modulating effect(s) thereof can then be evaluated by comparing the MGF-mediated response in the presence and absence of test compound, or relating the MGF-mediated response of test cells, or control cells (i.e., cells that do not express MGF), to the presence of the compound.

As used herein, a compound or signal that modulates the activity of MGF refers to a compound that alters the activity of MGF in such a way that the activity of MGF is different in the presence of the compound or signal (as compared to the absence of said compound or signal).

Also provided are recombinant proteins encoded by the above-described nucleic acids. The invention also relates to variants of said proteins, e.g. variants encoded by mRNA generated by alternative splicing of a primary transcript, as well as fragments thereof which retain one or more of the physiological and/or physical properties of MGF.

The MGF protein with the amino acid sequence set forth in SEQ ID NO: 2 has sequence homologies with the inteferon stimulated gene factors Stat91 and Stat113. Comparison of the MGF protein sequence with proteins in the EMBL data base show a distinct homology to the human ISGF-α proteins (Fu et al., (1992) *Cell* 74:1135–1145; Schindler et al., (1992) *Proc. Natl. Acad. Sci.*, 89:7836–7839). The overall identity between MGF and ISGF3 113 kDa and ISGF3 91 kDa is 28.5% and 29.2% respectively. Like the ISGF3 proteins, MGF contains a src homology 2 (SH2) like domain and a src homology 3 (SH3) like domain (Koch et al., (1989) *Mol. Cell. Biol.*, 9:4131–4140; Stahl et al., (1988) *Nature*, 332:269–272). Although MGF and the ISGF3-α proteins share homologies throughout, they also exhibit distinctive differences. The leucine zipper motif found in the ISGF3-α proteins is not present in the MGF sequence. MGF contains a putative tyrosine phosphorylation site at position 694 which is in the same relative position as the Stat91 and Stat113 (VDGYVKP; SEQ ID NO: 4, Shuai et al., (1993) *Science* 261, 1744–1746). This tyrosine can be phosphorylated by a protein tyrosine kinase (PTK) and regulate the MGF DNA binding activity. A highly conserved motif, GTFLLRFSXS (SEQ ID NO: 5), is found in the potential SH2 domain of MGF.

MGF from rat mammary glands has previously been purified to homogeneity by anion exchange chromatography on Bio-Rex 70, non-specific DNA- and sequence specific DNA affinity chromatography (Wakao et al., supra.). MGF from sheep mammary gland does not bind to the Bio-Rex 70 resin under the same conditions used for the purification of rat MGF. This indicates different charge properties of MGF from rat and sheep. NaCl is not sufficient to elute sheep MGF from the Red A resin, KSCN is used instead. KSCN shows a much stronger negative elution coefficient (Robinson et al., (1981) *Proc. Natl. Acad. Sci.*, 78:2287–2291), suggesting that sheep MGF is bound tightly to the Red A resin through ionic and hydrophobic interactions.

After the sequence specific DNA affinity column, two bands of 92 kDa and 84 kDa are detected by SDS gel electrophoresis. Only one band of 89 kDa is found after purification from rat tissue. This band is sufficient to form a specific protein-DNA complex in a bandshift experiment (Wakao et al., 1992). The 84 kDa protein is closely related to the 92 kDa protein and might originate from alternative splicing or proteolytic clipping. Both proteins have very similar DNA binding specificities and bind to the wild type MGF binding sequence and not to a mutated version. The relative abundance of the two proteins varies in different preparations. The 92 kDa protein usually is more abundant than the 84 kDa protein. The peptide patterns after in situ lysine C digestion are very similar. Both proteins are observed after in vitro transcription and translation of MGF cDNA.

The cDNA sequence (SEQ ID NO: 1) indicates that MGF belongs to a new family of transcription factors involved in the cytokine responses, the Stats (signal transducers and activators of transcription). The presence of SH-2 and SH-3 domains and the homologies to the Stat91 and the Stat113 of ISGF3 are noteworthy. SH-2 domains play a crucial role in protein-protein interactions and mediate the binding to phosphorylated tyrosine residues (Mayer and Hanafusa, (1990) *Proc. Natl. Acad. Sci.*, 87:2638–2642; Hirai and Varmus, (1990) *Mol. Cell. Biol.*, 10:1317–1317; Anderson et al., (1990) *Science* 250:979–982; Matsuda et al., (1991) *Science* 248:1537–1539; Mayer et al., (1992) *Mol. Cell. Biol.*, 12:609–618). The presence of a SH-2 domain within MGF suggests that MGF could interact directly with protein tyrosine kinases (PTK). Within the SH-2 domain of MGF there is a basic amino acid, lysine, at position αA2 like in other src family proteins. A basic amino acid at this position is highly conserved amongst different types of SH-2, and is directly involved in the interaction with phosphotyrosine (Waksman et al., 1992, 1993). MGF and ISGF3 proteins do not contain a region A. The region B present in ISGF3 proteins is absent in the SH-2 domain of MGF. Both regions are distinctive sequences for SH-2 containing proteins (Fu et al., supra., Schindler et al., supra.). It has been suggested that these sequences might be targets for PTKs.

The SH-3 domain of MGF also shares extensive homologies with the SH-2 domains of the ISGF3. MGF does not contain the YDYEE sequence which is conserved in many other SH-3 containing proteins. Although the role of the SH-3 domain is not unequivocally established, several functions have been proposed, such as cytoskeleton assembly and membrane rearrangement (Drubin et al., (1990) *Nature* 343:288–290; Rodaway et al., (1990) *Mol. Cell. Biol.*, 10:5388–5396). The DNA binding domain of MGF has yet to be identified. The DNA sequence to which MGF binds contains an imperfect palindrome, 5'-TTCNNNGAA-3' which might indicate that MGF binds to DNA as a homodimer. The DNA motif 5-TTC/ACNNNAA-3' is also present in the GAS element, the sequence to which Stat91 binds (Pearse et al., (1993) *Proc. Natl. Acad. Sci.*, 90:4314–4318) and in the APRF response element (Wegenka et al., (1993) *Mol. Cell. Biol.*, 13:276–288).

The cytokine and hematopoietic cell surface receptors do not have enzymatic kinase domains. Nevertheless, prolactin receptor activation induces tyrosine phosphorylation of several cellular proteins, e.g. p120, p97 and p40 (Rui et al., supra.). p120 is associated with the prolactin receptor and possibly itself a PTK. The PTK JAK2 is 130 kDa and associates with erythropoietin receptor (EPOR) and growth hormone receptor (GHR) (Witthuhn et al., supra.; Argetsinger et al., supra.). JAK2 is also activated by IL-3, GM-CSF, IFN-γ and prolactin (Silvennoinen et al., (1993) *Proc. Natl. Acad. Sci.* 90:8429–8433; Witthuhn et al., supra.). The data suggest that p120, which is tyrosine phosphorylation upon prolactin receptor activation, is JAK2. In IFN-γ signaling, JAK1 and JAK2 are responsible for the tyrosine phosphorylation of p91 (Shuai et al., supra.; Silvennoinen et al., supra.). JAK2 is also activated by IL-3, GM-CSF, and IFN-γ (Silvennoinen et al., supra.; Witthuhn et al., supra.). The similarity in molecular weight of the 97 kDa protein and MGF might be also indicative. A nuclear tyrosine phosphatase seems to be involved in the downregulation of interferon induced gene expression (David et al., (1993) *Mol. Cell. Biol.*, 13 7515–7521).

Only the long form of prolactin receptor activates the 92 kDa MGF. The short form of the prolactin receptor is unable to do so. The intermediate form of the prolactin receptor, missing 198 amino acids at its carboxyl terminus does not affect its signal transducing capacity (Ali et al., supra.; Russel, supra.). 160 amino acid residues of cytoplasmic domain are sufficient to transduce a signal. Similar deletion mutants have been reported for the IL-2 and EPO receptors (Hatakeyama et al., (1989) *Science* 244:551–556; D'Andrea et al., supra.).

It is important to analyse the phosphotyrosine residues in JAK2 and their interaction with SH-2 containing molecules. It is possible that MGF interacts directly with JAK2 via its SH-2 domain. A monoclonal anti-phosphotyrosine antibody detects three proteins, including p97, upon prolactin receptor activation. When antibodies against the prolactin receptor are used, p97 is not detected (Rui et al., supra.). This is indicative of MGF interaction with JAK2.

MGF has a putative tyrosine phosphorylation sequence RLGDLNY (SEQ ID NO: 6) at position 659 to 665. Mutation of this tyrosine will reveal whether this phosphorylation affects MGF DNA binding activity or translocation into the nucleus, similar to the situation reported for ISGF-α proteins upon IFN receptor activation (Shuai et al., supra.; Schindler et al., supra.; David and Larner, (1992) *Science* 2571, 813–815). The electrophoretic migration of the DNA protein complex formed by recombinant MGF from transfected COS cells is slightly different from that of the purified protein. This difference may be due to posttranslational modifications of MGF. MGF contains several putative PKC and CKII sites in addition to the potential phosphotyrosine site. The suppression of MGF activation and β-casein promoter induction by a selective inhibitor of PKC indicates additional regulatory phosphorylation events (Marte et al., (1994) *Cell Growth and Differentiation* in press). Other posttranslational modifications, glycosylation and myristylation, and their effects on MGF function will also have to be considered.

MGF activates a reporter gene in a prolactin dependent manner. The promoter of the reporter construct is a truncated rat β-casein gene comprising positions—334 to −1 (Schmitt-Ney et al., supra.). The co-transfection of MGF cDNA and the prolactin receptor into CHO cells, and prolactin induction results in a significant increase in the transcription of the reporter construct. MGF cDNA transfection or prolactin receptor transfection by themselves slightly increases the reporter gene promoter activity. Bandshift analysis shows that slightly increased levels of MGF DNA complex could be observed when MGF cDNA was transfected without the prolactin receptor construct. This might be attributed to the presence of small amounts of prolactin in the serum (Lesueur et al., supra.). Our results demonstrate that MGF can be directly activated by prolactin and transactivate a target gene. The MGF binding sequence is a prolactin response element.

In accordance with yet another embodiment of the present invention, there are provided antibodies generated against MGF, particularly MGF having the amino acid sequence set forth in SEQ ID NO: 2. Such antibodies can be employed for studying MGF tissue localization, screening of an expression library to identify nucleic acids encoding MGF, structure of functional domains, as well as in diagnostic applications, therapeutic applications, and the like. The antibodies (polyclonal or monoclonal) can be prepared employing standard techniques, as are well known to those of skill in the art, using the invention MGF protein or portions thereof as antigens for antibody production.

It is envisaged that transgenic animals, e.g. sheep, overexpressing MGF, can be produced e.g. in order to increase milk production or to produce sufficient amounts of a useful protein, e.g. a therapeutically useful protein.

The invention particularly relates to the specific embodiments as described in the Examples which serve to illustrate the present invention but should not be construed as a limitation thereof.

EXAMPLE 1

Purification of MGF

Nuclear extracts from the mammary tissue of lactating sheep are used as a source for the purification of MGF. MGF is purified by Red-A- and sequence specific DNA affinity-column chromatography. The purification is monitored by the bandshift activity of MGF as described previously (Schmitt-Ney et al., supra.).

Mammary gland tissue is obtained from sheep lactating for 4 days. The tissue is frozen in liquid nitrogen and stored at −70° C. All purification steps are done at 4° C. Nuclei are prepared as described previously (Wakao et al., supra.) and extracted with buffer D containing 400 mM NaCl. This fraction contains most of the MGF activity and is used for the purification. NP-40 is added to a final concentration of 0.1% (v/v). Nearly 100% of the MGF activity is recovered, very low MGF activity is recovered in the absence of NP40. After centrifugation of the MGF-fraction at 18000 r.p.m. in a SW21 rotor for 16 hours, the fraction is dialysed against buffer D (20 mM HEPES-NaOH pH 7.5, 50 mM NaCl, 2 mM EDTA, 1 mM DTT, 10% (v/v) glycerol, 0.1% (v/v) Nonidet P-40, and 0.2 mM PMSF). The specific MGF activity of the nuclear extract after dialysis is determined in a bandshift assay. One unit of MGF activity is defined as the amount which causes the retardation of 1 fmol of labeled DNA probe.

The dialysed nuclear extracts are applied to a Matrex gel Red A (Amicon) column (radius 15 mm×200 mm), pre-equilibrated with buffer D. After loading, the column is washed with three bed volumes of buffer D containing 300 mM NaCl and subsequently with the same volume of buffer D containing 50 mM KSCN. The column is developed with 800 ml of a linear gradient of 50–500 mM KSCN. 4 ml fractions are collected and 2 ml from each fraction are assayed for MGF DNA binding activity. MGF activity is eluted between 100 and 180 mM of KSCN. Positive fractions (180 ml) are collected and dialysed against 2 l of buffer D. Dialysed fractions are concentrated with Red A column (⅕ volume of the first column). MGF is eluted with 500 mM KSCN and dialysed against buffer E (10 mM Tris-HCl pH 7.5, 50 mM NaCl, 0.1 mM EDTA, 1 mM DTT, 5% (v/v) glycerol, 0.1% Nonidet P-40, and 0.2 mM PMSF). The eluate is concentrated to 20 ml after dialysis, and aliquots of 1 ml are stored at −70° C. KSCN is used to elute the column because poor recovery results after NaCl elution. Elution with 3M NaCl yields less than 10% of the applied activity.

Sequence specific DNA affinity chromatography is used for further purification. The promoter sequence of ovine β-casein is not yet known. Therefore, two MGF binding sequences, one from the rat β-casein gene (5'-GGACTTCT-TGGAATTAAGGGA-3'; SEQ ID NO: 7) and one from the bovine β-casein gene (5'-AGATTTCTAGGAAT-TCAATCC-3'; SEQ ID NO: 8) (Gorodesky et al., (1988) Gene 66:87–96) are compared for their ability to bind sheep MGF. The factor is found to bind more efficiently to the bovine sequence. The bovine β-casein MGF binding sequence is used in the bandshift and the affinity purification experiments.

A sequence specific DNA affinity column is prepared as described (Wakao et al., supra.), except the bovine β-casein MGF binding sequence is used. For the sequence specific DNA affinity column, 1 ml of material concentrated on Red A is mixed with the poly {d(I, C)} and poly {d(A, T)} (50 mg of each per mg of protein), incubated on the ice for 40 min and loaded onto 1 ml of the affinity column pre-equilibrated with buffer E. The sample is mixed with the DNA affinity resin and incubated for 45 minutes. The flow through is reloaded three times and the column washed with twenty volumes of buffer E containing 180 mM NaCl. MGF is eluted with 5 ml of buffer E containing 600 mM NaCl. 1 ml fractions are collected and 1 µl of each fraction is assayed for MGF activity.

MGF activity is eluted from the sequence specific DNA affinity column with buffer E containing 600 mM NaCl. Two bands of 84 kDa and 92 kDa are revealed when the eluates of 600 mM NaCl from the DNA affinity column are analyzed on SDS polyacrylamide gel electrophoresis and after silver staining. Both proteins possess similar DNA binding affinity. No further purification is achieved by selection on a DNA affinity column containing a point mutated MGF binding sequence followed by a column containing the wild type sequence.

EXAMPLE 2

Internal Amino Acid Sequencing

The eluate of the DNA affinity column is precipitated with TCA (trichloroacetic acid) at a final concentration of 17% (v/v) on ice for 2 hours. The precipitate is collected by centrifugation, and washed twice with ethanol/diethylether (1/1). The pellet is dried, the proteins are dissolved and separated by SDS gel electrophoresis. They are transferred onto a nitrocellulose membrane. The filter wash with NaOH is omitted. The proteins on the filter are visualized by staining with Ponceau S, the two bands of 92 kDa and 84 kDa are individually excised from the membrane. Protein sequencing is carried out at the Harvard Microchemistry facility. The proteins are digested in situ with the protease lysine C and the resulting peptides are separated by reverse phase chromatography. Amino acid sequence of individual peptides is determined with a ABI 477 A protein sequencer connected to a 120 A online PTH-amino acid analyser.

The peptide profiles of the two proteins obtained by reverse phase chromatography are almost identical. Peaks are pooled and subjected to amino acid sequence analysis. 2.2 pmol to 0.6 pmol of the amino acids residues are recovered after the sequencing reactions. Amino acid sequence is obtained for two peptides. The sequences of these peptides are QQTIILDDELIQWK (SEQ ID NO: 9) and YVKPQI (SEQ ID NO: 10), respectively (cf. SEQ ID NO: 2).

Based on the bias of human codon usage, a 42 bp oligonucleotide guessmer representing one of the peptides is synthesised (cf. Example 4) and used as a probe to screen a cDNA library.

EXAMPLE 3

Construction of a cDNA Library From the mRNA of Lactating Mammary Tissue

A cDNA library is constructed from mRNA of mammary gland of sheep lactating for 4 days. RNA is prepared and poly (A)+ RNA is selected. cDNA is synthesised with the Super Script lambda system cDNA synthesis kit (BRL), except EcoR1 adapters are used instead of Sal 1 adapters and lambdagt 11 phage instead of lambdagt 22A phage for the construction of the phage library.

EXAMPLE 4

Isolation of cDNA Clones Encoding MGF $6 \times 10^5$ phage clones of the cDNA library (Example 3) are screened with a guessmer derived from the 14 amino acid sequence of a peptide (cf. Example 2, supra). The sequence of this oligonucleotide is: 5'-TTCCACTGGATI-AGCTCITCITCIAGGATGATGGTCTGCTGT-3' (SEQ ID NO: 11) (I indicates inosine). The synthetic oligonucleotide is end labeled with {gamma $^{32}$P} ATP and T4 polynucleotide kinase and used to screen clones on Hybond N+ (Amersham). Prehybridisation is performed in 25 ml of solution containing 5×SSPE, 6% (w/v) polyethylenglycol M. W. 6000, 5×Denhard's solution, 0.5% SDS (w/v) and 500 mg of salmon sperm DNA at 37° C. under gentle agitation. Hybridisation is carried out for 16 hours at 45° C. in the same solution containing the radioactive probe. Filters are washed twice at room temperature in 2×SSPE and 0.1% (w/v) SDS for 10 minutes, then washed at 37° C. in 1×SSPE and 0.1% (w/v) SDS for 15 minutes. The washing temperature is increased to 48° C. in 1×SSPE and 0.1% (w/v) SDS. After the wash at 48° C. for 15 minutes, filters are autoradiographed and kept at −70° C. for 16 hours. After a second screening using the same oligonucleotide, 20 positive clones are isolated (frequency of 0.0004%). These clones are hybridised with another oligonucleotide: (5'-ATCTGIGGYT-TCACICCICCGTCCACIGCYTT-3' (SEQ ID NO: 12), Y indicates pyrimidines, and I indicates inosine) derived from the second peptide sequence obtained by microsequencing. All 20 clones hybridise with both oligonucleotides and are isolated as single plaques. These clones are subjected to restriction enzyme analysis and the DNA sequences of their 5' and 3' ends is determined.

Restriction enzyme analysis and partial DNA sequencing reveals that all clones represent the same mRNA. The sequence of clone 10 is determined as described below. This clone contains a cDNA insert of 2816 bp and a coding region of 2202 nucleotides. The cDNA and the deduced amino acid sequence of clone 10 is shown in SEQ ID NOS: 1 and 2, respectively. An open reading frame begins at position 244 and ends at position 2634. The open reading frame comprises 794 amino acids. The predicted molecular weight corresponds well with the observed molecular weight of the purified proteins. The two peptide sequences identified by protein microsequencing are present in this open reading frame (amino acid sequences of the peptides are set forth in Example 2). No poly A sequence is observed within the 3' non-translated region, suggesting the occurence of a natural NotI site. The cDNA of clone 10 is inserted in Blue Script KS+ using EcoRI and NotI sites.

DNA sequencing is performed as follows: the cDNA clones are sequenced using Sequenase TMkits from U.S. Biochemicals. Both strands of the clone 10 cDNA are sequenced. Synthetic oligonucleotides are used as primers. 5' and 3' deletion mutants are sequenced with T7 and a M13 universal primers. These deletion mutants are generated by Exo III limited digestion, using Erase Base kits from Promega. 5' deletion mutants are used for the in vitro transcription and translation experiments and for the construction of the eukaryotic expression vector (infra).

EXAMPLE 5

MGF Expression in Sheep Organs

Northern blot analysis of mRNA from different tissues is performed as follows: total RNA or polyA+ RNA is prepared from different organs of lactating sheep and separated on 1% agarose gel. RNA is transferred on the nylon filter and hybridised with the radio-labelled clone 10 fragment. Washing is performed with 0.1×SSC and 0.1% SDS at 60° C.

The highest expression of MGF mRNA is detected in sheep mammary gland. Two transcripts of 6.5 kb and 4.5 kb are found. The smaller form of 4.5 kb is predominant. MGF expression is not restricted to the mammary gland. MGF transcripts are also detected in ovary, thymus, spleen, kidney, lung, muscle, the adrenal gland and in cytotoxic T cells.

EXAMPLE 6

In Vitro Transcription and Translation of MGF cDNA

In vitro transcription is done with TNT T7 polymerase (Promega) and translation with a rabbit reticulocyte lysate according to the manufacturer's protocol. 1 µg of cDNA in Blue Script KS+ is used. The in vitro translated proteins are separated by SDS gel electrophoresis and autoradiographed. The size of the major in vitro translated protein is about 90 kDa. The in vitro translation efficiency depends absolutely on the 5' non-translated region. Very little in vitro translated protein is observed when the 5' non-translated region comprises 243 nucleotides. Deletion up to position −83 from the AUG initiation codon increases the translational efficiency. Deletion to position −23 results in even more efficient in vitro translation. The in vitro translated MGF is tested in a bandshift assay and shown to have no specific DNA binding activity. This is most likely due to the lack of protein phosphorylation (see below).

EXAMPLE 7

Transient Expression of cDNA Clones in COS Cells

A MGF expression vector is transfected into COS cells to confirm that the cloned cDNA encodes a sequence specific DNA binding protein. The clone 10 cDNA (BstBI cleaved, comprising nucleotides 222 to 2634) is inserted into the pXM eukaryotic expression vector. COS cells are grown in RPMI medium with 10% FCS. COS cells are transfected with 5 µg of pXM-MGF and 0.5 µg of the SV-40-β-galactosidase expression vector, and 5 µg of the pcDNAI vector containing the long or short form of the murine prolactin receptor. The total amount of DNA is adjusted with salmon sperm DNA to 20 µg. Transfection is performed by the calcium phosphate precipitation technique. 24 hours after transfection, COS cells are induced with 5 µM ovine prolactin. The cells are harvested 48 hours after transfection, and nuclear extracts are prepared. Gel retardation assays are performed as described by Wakao et al., supra. Endogenous MGF activity is not detected in COS cells. Low MGF activity is observed when COS cells are transfected with MGF cDNA. The treatment of the cells with prolactin does not significantly enhance MGF binding.

EXAMPLE 8

Activation of Recombinant MGF by the Long Form of the Prolactin Receptor

COS cells do not express prolactin receptor endogenously. To investigate the prolactin responsiveness of the recombinant MGF, MGF cDNA and two different forms of the prolactin receptor, the short form and the long form, are transfected into COS cells (cf. Example 7, supra). 24 hours after the transfection, the cells are induced with prolactin. Nuclear extracts are prepared 24 hours later, and analysed in bandshift assays. COS cells cotransfected with MGF cDNA and the long form of the prolactin receptor show a strong MGF DNA binding activity upon prolactin induction. Low MGF activity is found in the absence of prolactin. The cotransfection of the short form of the prolactin receptor fails to enhance MGF binding, independent of prolactin stimulation. The transfection of long and short form prolactin receptor alone results in no MGF binding. These observations are consistent with transfection experiments, which have shown that only the long form of the prolactin receptor confers milk protein induction and induces β-lactoglobulin gene transcription (Lesueur et al., supra.).

The specificity of the DNA binding is confirmed by oligonucleotide competition experiments. In the presence of a 100 fold molar excess of the wild type oligonucleotide, representing the MGF binding sequence, the MGF DNA complex is efficiently competed. In the presence of a mutated oligonucleotide, not capable of MGF binding, no competition is observed. These findings further confirm that the cloned cDNA encodes MGF and that the DNA binding of the recombinant protein can be activated directly by the long form of the prolactin receptor.

EXAMPLE 9

Prolactin Dependent Transactivation of a Reporter Gene Construct in CHO Cells Transfected with MGF cDNA CHO cells are grown in Optimem 1 medium (BRL) in the presence of 2% FCS. Transfection into CHO cells is performed in the same way as COS cells. 1.5 mg of the reporter gene (β-casein promoter-luciferase) is included.

The activation of the prolactin receptor induces the DNA binding activity of recombinant MGF in transfected cells. In order to test the ability of recombinant MGF to transactivate a reporter gene construct, MGF cDNA is cotransfected with a β-casein promoter-luciferase gene construct into CHO cells. A very slight increase in luciferase activity is detected when the β-casein promoter construct is cotransfected with the MGF cDNA or the long form of the prolactin receptor. Cotransfection of the promoter construct, the prolactin receptor and the MGF cDNA results in a substantial increase in luciferase activity which can be further enhanced by prolactin treatment of the transfected cells. These results demonstrate that recombinant MGF has the potential to activate transcription in transfected cells.

EXAMPLE 10

Phosphorylation of MGF

To investigate the effect of phosphorylation on MGF DNA binding activity using purified MGF from sheep mammary gland is used. MGF purified by DNA affinity chromatography is treated with the serine-threonine specific phosphatases PP1C and PP2A. No effect on the DNA binding activity of MGF is observed. Treatment of MGF with the tyrosine specific phosphatase PTP1B, however, abolishes DNA binding. Inclusion of vanadate, a potent protein tyrosine phosphatase inhibitor, in the dephosphorylation reaction prevents the loss of DNA binding activity. Recombinant MGF, activated by prolactin, from transfected COS cells is also tested. Tyrosine specific phosphatase treatment of nuclear extracts prevents the formation of the MGF-DNA complex. For this purpose, DNA affinity purified MGF is incubated with beads coupled to GST-fused PTP 1B (UBI) in buffer E, and used for bandshift analysis. The results show that MGF phosphorylation on tyrosine is essential for its DNA binding activity.

We claim:

1. An isolated DNA encoding mammary gland growth factor (MGF) consisting of the amino acid sequence set forth in SEQ ID NO: 2.

2. An isolated DNA encoding mammary gland growth factor (MGF) which has at least about 90% sequence identity to the nucleotide sequence set forth in SEQ ID NO: 1.

3. Isolated mRNA complementary to the DNA of either claim 1 or claim 2.

4. Host cells containing the DNA of either claim 1 or claim 2.

5. Host cells transcribing the DNA of either claim 1 or claim 2.

* * * * *